United States Patent [19]

Barnwell

[11] Patent Number: 5,391,377
[45] Date of Patent: Feb. 21, 1995

[54] BIPHASIC RELEASE FORMATIONS FOR LIPOPHILIC ACIDS

[75] Inventor: Stephen G. Barnwell, Chester, England

[73] Assignee: Cortecs Limited, Middlesex, England

[21] Appl. No.: 50,064

[22] PCT Filed: Oct. 18, 1991

[86] PCT No.: PCT/GB91/01824

§ 371 Date: May 10, 1993

§ 102(e) Date: May 10, 1993

[87] PCT Pub. No.: WO92/06680

PCT Pub. Date: Apr. 30, 1992

[30] Foreign Application Priority Data

Oct. 19, 1990 [GB] United Kingdom ............... 9022788

[51] Int. Cl.$^6$ .................................................. A61K 9/48
[52] U.S. Cl. ............................... 424/463; 424/476; 424/468
[58] Field of Search ............. 424/463, 78, 449, 485; 514/558; 546/318

[56] References Cited

U.S. PATENT DOCUMENTS

| | | | |
|---|---|---|---|
| 4,916,230 | 4/1990 | Alexander | 546/318 |
| 4,946,870 | 8/1990 | Partain | 424/449 |
| 5,229,422 | 7/1993 | Takahashi | 514/558 |

FOREIGN PATENT DOCUMENTS

| | | |
|---|---|---|
| 0255002 | 2/1988 | European Pat. Off. |
| 0351897 | 1/1990 | European Pat. Off. |
| 1600639 | 10/1981 | United Kingdom |
| 90/03164 | 5/1990 | WIPO |
| 90/12583 | 11/1990 | WIPO |

OTHER PUBLICATIONS

Singer et al., "Fish Oil Amplifies the Effect of Propranolol in Mild Essential Hypertension", *Hypertension*, vol. 16, No. 6, pp. 682–691 (Dec. 1990).

Moberly et al., "Oleic Acid Stimulation of Apolipoprotein B Secretion from HepG2 and Caco-2 Cells Occurs Post-Transcriptionally", *Biochimica et Biophysica Acta*, vol. 1042, pp. 70–80 (1990).

H. Nakamura, "Effects of Antihypertensive Drugs on Plasma Lipids", *The American Journal of Cardiology*, vol. 60, Sep., 1987, pp. 24E–28E.

W. Roberts, "Blood Lipid Levels and Antihypertensive Therapy", *The American Journal of Cardiology*, vol. 60, Sep. 1987, pp. 33E–35E.

(List continued on next page.)

*Primary Examiner*—Thurman K. Page
*Assistant Examiner*—William E. Benston, Jr.
*Attorney, Agent, or Firm*—Foley & Lardner

[57] ABSTRACT

A pharmaceutical formulation comprises: (a) a $C_{12}$–$C_{24}$ fatty acid, which may be saturated or mono- or polyunsaturated, such as oleic or linoleic acid; and (b) a generally lipophilic pharmaceutically active substance. A portion of the $C_{12}$–$C_{24}$ fatty acid is formulated for non-sustained release on non-parenteral administration and a portion of the $C_{12}$–$C_{24}$ fatty acid and at least a portion of the pharmaceutically active substance are formulated for sustained release on non-parenteral administration. The pharmaceutically active substance may be a cardiovascular drug such as propranolol, verapamil, nifedipine, diltiazem, metoprolol, nicardipine or labetolol. Such formulations promote absorption redistribution of the active substance(s) from the hepatic portal blood supply to the lymphatic system, thereby avoiding first-pass liver metabolism. Formulations of this type will have a predictable dose response in patients, achieved with a lower chemical load, with which therapeutic efficacy is maintained.

13 Claims, No Drawings

OTHER PUBLICATIONS

C. Pullinger, et al., "The Apolipoprotein B Gene is Constitutively Expressed in HepG2 Cells: Regulation of Secretion by Oleic Acid, Albumin, and Insulin, and Measurement of the mRNA Half-life", Journal of Lipid Research, vol. 30, 1989, pp. 1065–1077.

N. Dashti, et al., "Increased Production of Apolipoprotein B and its Lipoproteins by Oleic Acid in Caco-2 Cells" Journal of Lipid Research, vol. 31, 1990, pp. 113–123.

P. Greene, et al., "Facilitated Transfer of Cationic Drugs Across a Lipoidal Membrane by Oleic Acid and Lauric Acid," International Journal of Pharmaceutics, vol. 37, 1987, pp. 251-255.

R. Simpson, et al., "Significance of Non-esterified Fatty Acids in Iron Uptake By Intestinal Brush-Border Membrane Vesicles," Biochem. Biophys. Acta, 941, 1988, pp. 39–47.

J. Wrigglesworth, et al., "The Proteoliposomal Steady State", Biochem. J., 270, 1990, pp. 109–118.

Chemical Abstracts, 97:28538h, p. 306.

Chemical Abstracts, 94:145390c, p. 379.

Chemical Abstracts, 90:109849t. p. 377.

W. Gowan, et al., "The Effect of Solvent Composition Upon the Blood and Lymph Levels of Phenytoin in Rats After Gastric Administration," International Journal of Pharmaceutics, 28, (1986), pp. 193–199.

W. N. A. Charman, et al., "An Experimental system Designed to Study the In Situ Intestinal Lymphatic Transport of Lipophilic Drugs in Anesthetized Rats,", International Journal of Pharmaceutics, 33, (1986), pp. 155–164.

Charman, et al., "Testing Potential Dosage Form Strategies for Intestinal Lymphatic Drug Transport: Studies in the Rat," International Journal of Pharmaceutics, 33, 1986, pp. 173–179.

T. Tokumura, et al., "Enhancement of the Oral Bioavailability of Cinnarizine in Oleic Acid in Beagle Dogs", Journal of Pharmaceutical Sciences, vol. 76, No. 4, Apr., 1987, pp. 286–288.

BIPHASIC RELEASE FORMATIONS FOR LIPOPHILIC ACIDS

This invention relates to pharmaceutical formulations. In particular, the invention relates to a formulation for lipophilic drugs which may enhance the bioavailability of such drugs.

Many lipophilic pharmaceuticals, such as cardiovascular drugs, are subject to an extensive yet variable "first-pass" metabolism. This occurs because orally administered drugs absorbed from the gastrointestinal tract are transported in the hepatic portal blood supply directly to the liver. Since the liver is the major site of drug metabolism, and lipophilic drugs are more prone to rapid metabolism, a major portion of an absorbed lipophilic drug may be prevented from reaching the systemic circulation. Classes of drugs to which this consideration particularly applies involve lipophilic beta-blocking agents and calcium channel blocking agents. However, other classes of lipophilic drugs suffer high hepatic first-pass metabolism.

In the case of conventional dosage forms of drugs susceptible to the first-pass metabolism, the variability in hepatic first-pass metabolism between individuals or in the same individual at different times leads to an unpredictability in therapeutic response to a given drug dose. Determinants of the extent of hepatic first-pass metabolism include:

(i) the expression of genes which control the levels of drug metabolizing enzymes present in the liver;

(ii) an unpredictable or highly variable decline in the performance of hepatic drug metabolism in the elderly; and (iii) variability in the expression of drug metabolizing enzymes in children.

Lipophilic cardiovascular drugs, in particular beta-blocking agents and calcium channel blockers, are among those absorbed from the gastrointestinal tract into the hepatic portal blood system by a passive first order process. This absorption has been found to be virtually complete, but the drugs have been found to be subjected to variable and extensive metabolism before reaching the systemic circulation. The metabolism may be in the gastrointestinal lumen, the intestinal wall, or in the liver, but generally the liver is assumed to be the major site of this metabolism due to the virtually complete appearance of the drug in the hepatic portal vein. This metabolism of the drug during its first passage through the liver is called the "first-pass effect", as discussed above.

The first-pass effect has been reported frequently for lipophilic bases (e.g. propranolol) and esters of lipophilic acids (e.g. acetyl salicylic acid), but is uncommon for lipophilic acids (e.g. salicylic acid). Because of the extensive extraction or metabolism of the drug by the liver, these drugs exhibit bioavailabilies of less than 50%, together with a large variability in this parameter of a more than two-fold range.

Unpredictable hepatic drug extraction causes wide inter and intra subject variation in steady-state plasma drug concentrations in patients during chronic treatment, and hence it contributes to an unreliable dose response for a given drug. It is also apparent that drugs which undergo extensive first-pass metabolism may produce different plasma metabolite concentration versus time profiles after oral and parenteral administration.

It is generally found with lipophilic cardiovascular drugs that there is saturation of the metabolic pathways in the liver with increasing concentrations of drug in the hepatic portal blood supply. This saturation effect, which commonly occurs at the physiological concentrations encountered with normal dosing, is called the Michaelis-Menten effect and the drug is said to exhibit Michaelis-Menten kinetics.

When the drug concentrations in the hepatic portal vein are sufficiently low so as not to cause saturation of the metabolic pathways, or when the drug concentrations are so high as to cause total saturation of the metabolic pathways, then the pharmacokinetics are found to be linear. This means that the amount of drug entering the systemic circulation is proportional to the dosage. In the case of saturation of the metabolic pathways, a threshold dose is required to saturate the metabolic pathways before linearity is apparent.

When Michaelis-Menten kinetics are in effect, then the pharmacokinetics are non-linear, as increasing the dose increases the degree of saturation of the metabolic pathways causing a disproportionate increase in bioavailability. This property leads to difficulty in titration of dosage.

The bioavailability of some drugs that are subject to extensive first-pass metabolism after administration of a single dose increases when the drugs are given chronically. This non-linearity is most probably due to saturation of metabolism at the higher drug concentrations achieved during repeated administration.

The faster the release of a drug into solution in the small intestine, the more likely that saturation will occur and the greater will be the saturation effect, leading to increased bioavailability. Conversely, the slower the release, the more likely that saturation will not occur and hence the first-pass effect will be at a maximum. Thus sustained release preparations generally have lower bioavailability than rapid release preparations.

Cardiovascular drugs which are particularly suitable for delivery using the present invention include the beta-blockers propranolol, metoprolol, labetolol, oxprenolol, timolol and acebutolol, together with the calcium channel antagonists nifedipine, diltiazem, nicardipine and verapamil. These drugs are all characterised by their extensive first-pass clearance and metabolism, unlike the hydrophilic beta-blockers atenolol and nadolol, which are not extensively metabolised by the liver. In overall terms, suitable drugs for delivery using the present invention are best described as being subject to high hepatic first-pass clearance and metabolism, resulting in a low systemic bioavailability after oral dosing, and are available in a physical state compatible with the components of the delivery system (e.g. the drug molecule is presented as a base rather than a hydrochloride).

Verapamil and diltiazem show linear pharmacokinetics (no Michaelis-Menten saturation of first-pass metabolism) for single dosing, but saturation and increased bioavailability with multiple dosing. Propranolol and metoprolol show linear pharmacokinetics in single and multiple dosing. Nifedipine exhibits linear pharmacokinetics such that multiple-dose behaviour can be predicted from a single dose profile.

Non-linear pharmacokinetics for a drug mean that sustained release formulations of the drug effectively require higher daily doses than conventional rapid release preparations. This has been assumed to be acceptable because of the benefits of reduced side-effects in the early post dose period with some drugs, and the need for less frequent dosing.

Nifedipine provides an example of a drug which exhibits side-effects such as flushing and tachycardia in some patients, with most of these effects being considered to be related to the drug's pharmacokinetic profile. The conventional dosage forms must be dosed either twice or three times daily which can produce significantly fluctuating peak and trough concentrations. In order to reduce these side-effects and also, more importantly in fact, to reduce the number of daily doses, slow release tablet formulations of nifedipine have been developed.

There is therefore a need, for the drugs specifically mentioned above and other lipophilic drugs, for a pharmaceutical delivery system which improves bioavailability and overcomes the problems associated with non-linear pharmacokinetics.

WO-A-9012583 provides pharmaceutical formulations which do improve the bioavailability of certain lipophilic pharmaceutically active agents, including cardiovascular drugs. That application uses a natural mixture of bile components as excipients. Although the formulations work well, it is preferable for some purposes to have a more precisely defined pharmaceutical formulation. It would also be advantageous to improve upon these prior compositions.

WO-A-9003164 discloses two-phase pharmaceutical formulations of hydrophilic pharmaceutically active agents including insulin, calcitonin and somatotropin. Oleic acid is among the materials that can be included in the relatively complex formulations disclosed, but in view of the lipophilic nature of oleic acid and the hydrophilic nature of the active ingredients, the oleic acid and active ingredients will partition substantially in different phases.

The present invention relates to a different approach for formulating lipophilic pharmaceutically active substances.

According to a first aspect of the present invention, there is provided a pharmaceutical formulation comprising:

(a) a $C_{12}$–$C_{24}$ fatty acid;
and (b) a pharmaceutically active substance;

wherein a portion of the $C_{12}$–$C_{24}$ fatty acid is formulated for non-sustained release on non-parenteral administration and wherein a portion of the $C_{12}$–$C_{24}$ fatty acid and at least a portion of the pharmaceutically active substance are formulated for sustained release on non-parenteral administration.

It is believed that such a formulation diverts a significant part of the absorption of the pharmaceutically active substance to the lymphatic absorption pathway, thereby leading to a major reduction in the quantity of drug entering the hepatic portal vein, and hence a reduction in the first-pass effect for subjects who would demonstrate high hepatic metabolism of the drug.

The part of the lymphatic system which drains from around the gastrointestinal tract has an important role in that it functions as a vehicle for the transport of certain lipid soluble nutrients. These materials, which include the fat soluble vitamins A, E, D, K, cholesterol and long-chain fatty acids, are carried in lymph mainly within or associated with lipoproteins. The lipoproteins, either very low density lipoproteins or chylomicrons, are manufactured by the absorptive enterocytes and exported into the lymph from where they gain direct access to the systemic blood supply without an initial passage through the liver. In comparison, molecules which are relatively more hydrophilic in nature and/or of lower molecular weight than those found in the lymph pass into the capillary bed surrounding the gastrointestinal tract and then circulate in the blood to the liver via the hepatic portal vein. Initial passage through the liver before reaching the systemic blood provides an opportunity for metabolic modification.

Component (a) of a formulation of the invention is a $C_{12}$–$C_{24}$ fatty acid. The fatty acid may be saturated or unsaturated. A preferred unsaturated acid is stearic acid ($C_{18:0}$). An unsaturated acid may be mono-unsaturated or poly-unsaturated. A preferred mono-unsaturated fatty acid is oleic acid ($C_{18:1}$). Preferred poly-unsaturated fatty acids include linoleic acid ($C_{18:2}$) and linolenic acid ($C_{18:3}$).

Arachidonic acid (an Omega W6 fatty acid) is an important metabolic precursor for the series 2 prostaglandins which have powerful effects on smooth muscle contractions and blood platelet aggregation. Docosohexanoic acid ($C_{22}:6W3$) is an Omega 3 essential fatty acid, derived from fish oil, which has been found to inhibit blood platelet aggregation and have favourable effects on cardiovascular risk factors by increasing the amount of high density lipoprotein (HDL) relative to Low Density Lipoprotein (LDL). A number of potential benefits may be obtained from co-administering these fatty acids with pharmaceutical bases. For example, it is well documented that $\beta$-blocker therapy causes unfavourable changes in blood lipoproteins which may increase cardiovascular risk (Nakamura, H, A., J. Cardiol, 1987, 60, 24E–28E; Roberts, W. C., Am; J. Cardiol, 1987, 60, 33E–35E). It is therefore likely that formulation of $\beta$-blockers in fatty acids of this type could help to reduce these adverse effects. Studies using conventional propranolol treatment in tandem with fish oil therapy have observed a potentiation of the blood pressure lowering effects of propranolol (P. Singer, S. Melzer, M. Goschel and S. Augustin. Hypertension 1990, 16, (6) 682–691). However, the biphasic formulations of the present invention, and the advantages that flow from their use, are neither disclosed nor suggested.

Fatty acids may be present individually or in combination with each other. They may be present either as the free acid or as a salt with a pharmaceutically acceptable cation, such as calcium or sodium.

Component (b) of a pharmaceutical formulation in accordance with the invention is a pharmaceutically active substance, which will generally be lipophilic and which is for preference soluble in the fatty acid. It is not of course necessary for the pharmaceutically active substance to be infinitely soluble in the fatty acid under all conditions; rather, it is preferred that the pharmaceutically active substance have sufficient solubility in the fatty acid to enable pharmaceutical formulations to be readily prepared. The amount dissolved will generally be related to the effective dose. Having said that, however, it is preferred that the pharmaceutically active substance be present in the form such that it will readily dissolve in the fatty acid carrier. Typically, the drug will be in the form of a base, but salts are not excluded. Under some conditions, it is possible that a fatty acid salt, ester, amide or other compound may be formed with the pharmaceutically active substance. Mixtures of different active substances may be formulated by means of this invention.

The lipophilicity of a drug may be assessed by its octanol/water partitioning coefficient, which is believed to give an approximation to its membrane permeability. A log p value of at least 2 usually indicates a drug which is sufficiently hydrophobic or lipophilic for significant targeting to the hydrophobic central nervous system compartment of the body.

Drugs in general which are subject to high hepatic first-pass clearance and metabolism may be formulated in accordance with the present invention provided that they are available in a compatible physical form. However, a particularly preferred formulation includes the cardiovascular drugs propranolol, metoprolol, timolol, verapamil and diltiazem present as free base. Other drugs may be preferred, for example nifedipine, nitrendipine, felodipine and nimodipine.

Other drugs which are subject to first pass metabolism and are particularly suitable candidates for formulation by means of the present invention include, but are not limited to, labetolol, nicardepine, oxypentifylline, oxprenolol, adrenalin, dopamine, fenoterol, ibopamine (SK&F 100168), orciprenaline, phenylephrine, rimiterol, ritodrine, salbutamol, terbutaline, fenoldopam (SK&F 82526), imipramine and trimipramine.

In general, calcium channel antagonists, $\beta$-blockers, $\beta^2$-agonists (especially salbutamol) and tricyclic antidepressants may be suitable candidates for formulation by means of the invention.

The pharmaceutically active substance may be in the form of a pro-drug. Examples of such pro-drugs include esters and amides formed by reaction (whether prior to or after incorporation into the pharmacuetical formulation) between the fatty acid and the pharmaceutically active compound. An ester may be formed when the pharmaceutically active compound has a suitable hydroxyl group, and an amide may be formed when the pharmaceutically active compound has a suitable primary or secondary amine group.

As stated above, a portion of the $C_{12}$–$C_{24}$ fatty acid is formulated for non-sustained (and usually rapid) release on non-parenteral (generally oral) administration and a portion of the $C_{12}$–$C_{24}$ fatty acid and at least a portion (but in some cases all) of the pharmaceutically active substance are formulated for sustained release on non-parenteral (again, generally, oral) administration. Formulations in accordance with the invention therefore have a biphasic release profile.

It is believed that pharmaceutically active substances which are conventially formulated or sought to be formulated for sustained release will get the greatest benefit from the invention, as drugs so formulated would be subject to maximum metabolism when passing through the liver. This is because they are delivered to the liver at low concentrations, such that the metabolic pathways are unsaturated. Diversion of absorption to the lymphatic absorption pathway should therefore lead to a substantial increase in bioavailability.

The expression "sustained release" is well understood in pharmaceutical formulation chemistry and needs no special definition. Generally, though, a pharmaceutically active agent may be said to be released sustainedly if it is released over or within a period of at least 30 minutes and preferably at least 1, 2, 5 or even more hours. A sustained release formulation may also be (but does not have to be) a delayed release formulation.

The non-sustained release portion of the $C_{12}$–$C_{24}$ fatty acid may be present on its own or in a relatively simple formulation. If pharmaceutically active substance is present in the non-sustained release portion, it may be mixed with or, for preference, dissolved in the $C_{12}$–$C_{24}$ fatty acid. Although there is no reason in principle why this portion of the overall formulation cannot be formulated in a more complex matter to suit particular circumstances (for example, a rapid release preparation may also take the form of granules containing the fatty acid and pharmaceutically active substance), the simplest formulation strategy will often be preferred.

The proportion of fatty acid to pharmaceutically active ingredient in the non-sustained release phase will vary from formulation to formulation. Generally, the ratio (weight:weight) of fatty acid to active ingredient will be in the range from 10:1 to 0.1:1, with from 5:1 to 1:1 being preferred.

A portion of the $C_{12}$–$C_{24}$ fatty acid and a portion (or, if none is available for non-sustained release, all) of the pharmaceutically active agent is formulated for sustained release. There are a number of different formulation approaches which can be used to achieve this property. First, the component(s) for sustained release can be granulated, such as by the use of cellulose derivatives (of which hydroxypropyl cellulose is an example) or gums; granulation technology is well known in the art. The granules may then be provided with a sustained release coating, such as ethyl cellulose. The coated granules may then be dispersed in the non-sustained release phase of the formulation.

A different approach is to formulate the component(s) for sustained release as an erodible and/or thermosoftening solid (at physiological temperatures). For this purpose, the component(s) for sustained release may be mixed with one or more glycerides or other suitable and physiologically compatible compounds having a transition temperature (melting point) above 37° C. Suitable glycerides include di- and tri-glycerides, such as many of the various GELUCIRE compounds, which are hydrogenated fatty acid esters available from Gattefosse. (The word GELUCIRE is a trade mark.) Other trade marks of suitable glycerides include LABRAFIL and PRECIROL. GELUCIRE compounds and other suitable compounds having transition temperatures of from 45° C. to 70° C. are preferred. Specific examples of exemplary GELUCIRE compounds, and their equivalents include:

GELUCIRE 50/02
GELUCIRE 54/02 (also available as PRECIROL)
GELUCIRE 62/05 and
GELUCIRE 64/02 (also available as PRECIROL WL 2155).

(The first two digits in the numeric portion of the GELUCIRE name represent the liquid/solid phase transition temperature in degrees centigrade and the second two digits represent the hydrophile/lipophile balance (HLB) value. Low HLB values (for example 6 or 5 or below) for the GELUCIRE compounds are preferred, not least because those GELUCIRE compounds with the most appropriate phase transition temperatures tend to have low HLB values and also because low HLB GELUCIRE compounds have more appropriate water dispersibility properties in the context of the invention. However, the use of other GELUCIRE compounds, which do not have the preferred characteristics set out above, may additionally be used as modifiers of sustained release rates.

Various formulation aids may be present. For example, a surfactant, such as one or more of those discussed below in more detail, may be included in the sustained release phase of the formulation. Surfactants are useful in manufacturing as they can help components co-solubilise and tend to reduce bubbling if the formulation is introduced into a capsule. Additionally, surfactants may help with the erodibility characteristics of the sustained release phase in vivo. Another formulation aid which may be present is a fluidiser and/or thickening agent. A silicon dioxide preparation which fulfills both these roles is available under the trade mark AEROSIL (for example AEROSIL 200). The silicon dioxide component may also have a beneficial effect on the erodibility characteristics of the formulation.

A further approach to formulating the component(s) for sustained release is to use a thixotropic material. Such materials behave as fluids when stressed by shearing forces (such as may be induced by stirring or pumping) but become non-flowing gels when the shearing force is removed. Like thermosoftening vehicles, described above, thixotropic vehicles are well suited to hard gelatin encapsulation technology. Suitable thixotropic vehicles include colloidal silicon dioxide (such as the AEROSIL 200 preparation previously referred to) and ethyl cellulose (also previously referred to as a sustained release coating agent). In this embodiment of the invention it is contemplated that the thixotropic vehicle is mixed with the component(s) for sustained release. Other components which may be present include gel promoters and dispersion aids. Glycols such as polyethylene glycol (for example PEG 400) are useful gel promoters in thixotropic formulations and also assist dispersion. Non-ionic surfactants, such as polyethoxylated, optionally hydrogenated, castor oil, for example having HLB values in the range 12 to 14 or 14 to 16, may be used.

The gel composition may be varied within quite wide limits while retaining accepatble performance. The following factors on the physical characteristics is given below.

i 1–2% glycol such as PEG 400 is sufficient to produce a firm gel with reasonable dispersion behaviour. The exclusion of such a glycol may yield a formulation with more of the characteristics of a viscous oil and the dispersion is not so good.

ii Increasing the AEROSIL or similar component up to 10% form the apparent optimum of about 6% results in a very firm gel without adversely affecting the dispersion. However, the rigid nature of gels containing high levels of AEROSIL may cause manufacturing problems on a larger scale.

iii Increasing the concentration of the pharmaceutically active substance (for example propranolol) above 20% may cause a softening of the gel (i.e., diminish the structure). The dispersion behaviour may be adversely affected also. So it is preferred to keep the concentration of the active substance below 20% (w/w).

As was the case with the non-sustained release phase, the proportion of fatty acid to pharmaceutically active ingredient in the sustained release phase will vary from formulation to formulation. Generally, the ratio (weight:weight) of fatty acid to active ingredient will be in the range from 10:1 to 0.1:1, with from 5:1 to 1:1 being preferred.

Formulations in accordance with the invention may, as alluded to above, be introduced into hard or soft gelatin capsules. Hard gelatin capsules may be preferred; when hard gelatin capsules are used and the formulation filling them contains one or more surfactants, it may be desirable to prevent embrittlement of the hard gelatin shell to incorporate anti-embrittlement additives, as suggested in WO-A-9102520.

It is not necessary for any other ingredient to be present. However, in some cases it may be useful to add one or more antioxidants to protect unsaturated double bonds present in the fatty acid. Suitable antioxidants include d-$\alpha$-tocopherol, dl-$\alpha$-tocopherol, butylated hydroxytoluene (BHT) and butylated hydroxyanisole (BHA). Antioxidants can be used either singly or in combination.

Another optional ingredient is a surfactant, as briefly mentioned above. Suitable surfactants are either ionic or nonionic, but in general do not include bile acids or their salts. Nonionic surfactants are preferred. A suitable HLB range for the surfactant, if present, is broadly from 0 to 20, preferably from 6 to 18 and typically from 10 to 18. Examples of suitable surfactants, which may be used singly or in combination, include the polyoxyethylene sorbitan fatty acid esters (e.g. polysorbate 80, polysorbate 60, polysorbate 40, polysorbate 20), the polyoxyethylene stearates (e.g. polyoxyl-40 stearate) and the polyoxyethylene, optionally hydrogenated, castor oil derivatives such as the CREMOPHOR RH40 and EL products.

It is generally preferred that pharmaceutical formulations in accordance with the invention be substantially non-aqueous, in the sense that no water is added. Some water may be present in the ingredients used. However, water-free formulations need not be preferred for all applications.

Formulations in accordance with the invention may be enteric coated or otherwise protected to ensure better survival of the pharmaceutically active compound through the stomach. Any convenient enteric protection method may be used. Capsules containing the formulation may be coated with an enteric coat such as hydroxypropyl methylcellulose phthalate or by the commercial coating process of Pharma-Vinci P/S.

Formulations of this invention are designed to promote absorption redirection of lipophilic drugs into the lymphatic system because of several factors. First, lipophilic drug entities by virtue of their greater solubility in lipid systems will have a predisposition to be absorbed via the lymphatic system. Secondly and similarly, long-chain fatty acids are mainly absorbed from the gastrointestinal tract into the lymphatic system. Finally, and most importantly, unsaturated fatty acids including oleic acid and linoleic acid have the important biochemical property of being able to act in a hormone-like fashion and switch on the secretion of chylomicrons from enterocytes and promote the formation of lymph. Thus, formulations in accordance with the invention are believed to function in the following way: fatty acid and the lipid soluble drug are released from a suitable dosage form and are absorbed by the enterocytes surrounding the gastrointestinal tract. Due to the lipophilic nature of the drug it has an innate tendency to be treated as a lipid and therefore predisposed to be sorted for lymphatic secretion by the enterocytes. The presence of oleic acid or other fatty acid provides ample material for the synthesis of triglycerides and other material also destined for the lymph within lipoproteins, mainly chylomicrons. It is believed at this stage the drug becomes associated with, or incorporated within, the lipoproteins destined for the lymph. Furthermore, a fatty acid such as oleic acid then acts as a biochemical messenger, switching on chylomicron export into the lymphatic system. The drug is therefore carried directly to the systemic circulation, via the lymph, avoiding the liver.

The regulation of lipoprotein metabolism on the molecular level is not well understood. In particular the role of dietary fatty acids in controlling the synthesis and secretion of chylomicrons, very low density lipoproteins, low density lipoproteins and high density lipoproteins is unknown. In vitro models for liver and intestine, using the HepG2 and Caco2 cell lines grown in culture respectively, have been used to try and elucidate these metabolic processes.

The studies of Pullinger et al (J. Lipid Research 1989, 30 1065–77), Moberley et al (Biochim. Biophys. Acta 1990, 1042 70–80) and Dashti et al (J. Lipid Research 1990 31 113–123) have shown that oleic acid increases the synthesis of apolipoprotein B (apoB) and its secretion by both HepG2 and Caco-2 cells. It is likely that stimulation occurs post-transcriptionally and is probably a co- or post-translational event. The effect of oleic acid has been shown to be dose dependent up to a threshold concentration of 1 mM in cell culture by Moberley et al.

Green and Hadgraft (International J. Pharmaceutics 1987 37 251–255) used an artificial membrane system to show that oleic acid facilitated the absorption of cationic drugs including metoprolol, oxprenolol and propranolol via an ion pair mechanism. The ability of oleic acid to facilitate uptake into vesicles containing membranes from intestinal brush border has also been demonstrated by Simpson et al (Biochim. Biophys Acta 1988 941 39–47).

Further studies have shown that oleic acid can act as an H+ ionophore which promotes the acidification of intracellular compartments (Wrigglesworth et al Biochem J. 1990 270 109–118), a process which is associated with the budding of secretory vessels.

It is likely that fatty acids such as oleic acid used in this invention are acting in a hormone-like fashion capable of switching on the synthesis and secretion of chylomicrons and other lipoproteins by the absorptive cells surrounding the gastrointestinal tract. Furthermore, the presence of fatty acid in close association with the membranes of the cells surrounding the gastrointestinal tract will enhance the absorption of pharmaceutical bases by an ion pairing effect. This effect would be potentiated by the use of the free base of the drug since this would allow co-dissolution in the dosage form, close association upon release from the dosage form, and enhance the ion pairing effect of oleic acid at the membrane. It should be noted though that the observed efficacy of formulations of the invention is not dependent on the correctness of these hypotheses.

Pharmaceutical bases are readily soluble in unsaturated fatty acids such as oleic acid and linoleic acid and docosohexanoic acid.

Formulations of the present invention, by virtue of their ability to avoid hepatic first-pass metabolism, may allow a substantial reduction of typically 50% in the dose of administered drug. This reduction in chemical load may be achieved while maintaining the same therapeutic levels of drug in the systemic circulation as found using the standard drug formulation presently available. Furthermore, the levels of drug present in the systemic circulation after administration in formulations of the present invention may be subject to less variation than conventional drug formulations. It is likely that the more predictable dose response achieved in patients will lead to a greater confidence in therapeutic efficacy. Therefore patients' symptoms may be able to be controlled more quickly and easily with reduced side effects and toxicity risk.

Pharmaceutical formulations in accordance with the invention may be prepared by any convenient method. According to a second aspect of the invention, there is provided a process for the preparation of a pharmaceutical formulation as described above, the process comprising preparing non-sustained release and sustained release phases, wherein the non-sustained release phase contains a portion of the $C_{12}$–$C_{24}$ fatty acid and wherein the sustained release phase contains a portion of the $C_{12}$–$C_{24}$ fatty acid and at least a portion of the pharmaceutically active substance, and formulating the non-sustained release and sustained release phases together.

In preferred embodiments, the pharmaceutically active substance is disolved in the fatty acid. It may be necessary or desirable to apply heat, depending on the exact nature of the substances involved. A clear solution is indicated by the absence of any undissolved particles.

According to a third aspect of the present invention, there is provided the use of a formulation as described above in the preparation of a medicament for the treatment of a disease or condition manageable by the pharmaceutically active substance. In some embodiments, the disease or condition is cardiovascular, and the pharmaceutically active substance is a cardiovascular drug. It can be seen that the invention can therefore be used in a method of treating a disease or condition manageable by the pharmaceutically active substance, particularly in cardiovascular cases as indicated above.

Preferred aspects of this and the other aspects of the invention are as for the first aspect, mutatis mutandis.

The invention will now be illustrated by the following examples. Proportions are w/w, unless otherwise stated.

EXAMPLE 1

The following is an example of a sustained release system incorporating a rapid release and slow release component. The slow release component is an example of a thermosoftening vehicle. Typically these materials melt upon heating thereby allowing the use of conventional mixing and pumping technology for fluid filling.

A. Slow Release Component

| Material/Quantity | | mg/capsule |
|---|---|---|
| Oleic acid B.P. | 40.0 g | 100.7 |
| GELUCIRE G50/02 | 37.5 g | 93.3 |
| CREMAPHOR RH40 | 11.0 g | 27.2 |
| Propranolol | 16.0 g | 40.0 |
| AEROSIL 200 | 4.8 g | 10.0 |

The oleic acid, GELUCIRE and CREMAPHOR were heated to 50°–55° C. until a clear solution was obtained. Propranolol base was added with stirring, while maintaining the temperature of the mix at 50° C., and continued until the propranol base was fully dissolved. Finally AEROSIL was added while stirring. A total of 274 mg of the formulation was filled into size '1' hard gelatin capsules while hot and then allowed to solidify with cooling.

The equivalent dose contained in the partially filled capsules at this stage was 40 mg of propranolol.

B. Rapid Release Component

| Material/Quantity | | mg/capsule |
|---|---|---|
| Oleic Acid B.P. | 43.4 g | 108.5 |
| Propranolol Base | 16.0 g | 40.0 |
| d-alpha-Tocopherol | 0.6 g | 1.5 |

Oleic acid and d-alpha-tocopherol were heated with stirring at 45°–50° C. Propranolol was added and dissolved with stirring. A total of 154 mg of the formulation was then added to the size '1' hard gelatin capsules already containing the solidified slow release component. The combined total dose per capsule was 80 mg of propranolol. The resulting capsules containing a solid sustained release plug covered by the liquid rapid release component. (A small manufacturing overage is included in the fill weights).

C. Enteric Coating Procedure

The sustained release capsules are enteric coated as described below.

To protect the composition from the acid environment of the stomach, and to delay the release of the contents until the dosage form was present in the duodenum, an enteric coating was applied to the hard gelatin capsules.

The enteric coating material used was hydroxypropyl methylcellulose phthalate (HP55 by Shin-Etsu) and was applied using the following solution after sealing the contents of the capsules using a LICAPS® test kit supplied by Capsugel. (The word LICAPS is a trade mark.)

The enteric coating solution contained:

| HP55 | 6.0% |
|---|---|
| Ethanol | 84.5% |
| Purified water | 9.5% | and was applied using a UNIGLATT fluidized bed system. (The word UNIGLATT is a trade mark.)

EXAMPLE 2—Dissolution Studies

For evaluating the dispersion behaviour of the experimental formulations a test method was devised based upon the USP XXII dissolution test for tablets and capsules. The aim of the test was to subject the samples to an environment similar to that in the intestine. Dispersion in 5 hours was selected as a satisfactory total release time for the test samples. This was based on the understanding that lymphatic absorption occurs predominantly in the small intestine.

The dissolution apparatus as specified by the USP XXII (apparatus 2) was used with Sorensens phosphate buffer, pH 6.8 containing 0.2% sodium cholate and 0.1% sodium deoxycholate, equilibrated to 37° C. The total volume of buffer added to each dissolution vessel was 900 ml with a paddle rotation speed of 75 rpm. The paddle height was adjusted so that the top edge of the blade was level with the surface of the liquid. The test sample was dropped into the dissolution medium and the rotation of the paddle started. The test sample was allowed to float freely at the liquid surface throughout the test. At each time-point a 5 ml aliquot of the dissolution medium was removed and replaced with 5 ml of fresh buffer solution. The sampled aliquot was diluted with 5 ml of methanol and the resulting solution passed through a 0.8 μM membrane filter (Sartorius, Minisart NML) prior to determining the absorbance at 290 nm using a UV-visible single beam spectrophotometer. The propranolol concentration in the dissolution medium was calculated using a pre-determined calibration curve data for propranolol.

| Dissolution Study Using Example 1 Formulation | | |
|---|---|---|
| | % Propranolol Release | |
| Time (h) | pH 1.2 | pH 6.8 |
| 0 | 0 | 0 |
| 0.5 | 0 | 42 |
| 1.0 | 0 | 60 |
| 2.0 | 0 | 75 |
| 3.0 | N.D. | 80 |
| 4.0 | N.D. | 87 |
| 5.0 | N.D. | 96 |

Values represent means of six determinations; N.D. = Not Determined.

The dissolution study using the Example 1 formulation results in total drug release in five hours. This is achieved with the initial rapid release of the oily component of the formulation followed by the gradual erosion of the waxy matrix. Release of the propranolol by erosion is important to ensure that oleic acid is released simultaneously with propranolol in the gastrointestinal tract thereby enhancing lymphatic uptake. Dissolution studies carried out at pH 1.2 indicated that the enteric coating applied to the capsules remained intact for the 2 hour test period used.

EXAMPLE 3

The following formulation was prepared:

| Oleic acid B.P. | 73% |
|---|---|
| Propranolol base | 20% |
| Aerosil 200 | 6% |
| PEG 400 | 1% |

The gel was prepared by dissolving propranolol base in oleic acid and PEG 400, at 50° C. Aerosil was then added until a homogeneous gel was formed.

I claim:

1. A biphasic pharmaceutical formulation comprising:
   (a) a sustained release component consisting essentially of a fatty acid moiety of at least one $C_{12}$–$C_{24}$ fatty acid and a pharmaceutical moiety; and
   (b) a non-sustained release component comprising at least one $C_{12}$–$C_{24}$ fatty acid;
   wherein the fatty acid of (a) and (b) may be the same or different.

2. A formulation as claimed in claim 1, wherein the fatty acid comprises oleic acid and/or linoleic acid.

3. A formulation as claimed in claim 1, wherein the pharmaceutically active substance is in the form of a base.

4. A formulation as claimed in claim 1, wherein the pharmaceutically active substance is a cardiovascular drug.

5. A formulation as claimed in claim 1, wherein the pharmaceutically active substance is selected from the group consisting of propranolol, verapamil, nifedipine, diltiazem, metoprolol, nicardipine and/or labetolol.

6. A formulation as claimed in claim 1, wherein said non-sustained release component further comprises the pharmaceutically active substance.

7. A formulation as claimed in claim 6, wherein the sustained release characteristics are afforded by erodible and/or thermosoftening material.

8. A formulation as claimed in claim 1, further comprising an antioxidant.

9. A formulation as claimed in claim 1, further comprising a surfactant.

10. A formulation as claimed in claim 9, wherein the surfactant is polysorbate 80 and/or POE-40 stearate.

11. A formulation as claimed in claim 1, wherein said formulation is substantially non-aqueous.

12. A process for the preparation of a pharmaceutical formulation, the process comprising preparing non-sustained release and sustained release components, wherein the non-sustained release component comprises at least one $C_{12}$–$C_{24}$ fatty acid and wherein the sustained release consists essentially of at least one $C_{12}$–$C_{24}$ fatty and a pharmaceutically active substance, wherein the non-sustained release and sustained release fatty acids may be the same or different.

13. A process as claimed in claim 12, the process comprising dissolving the pharmaceutically active substance in the fatty acid.

* * * * *